United States Patent
Behrends et al.

(10) Patent No.: US 6,903,210 B2
(45) Date of Patent: Jun. 7, 2005

(54) WASHING DISINFECTANT FOR HYGIENIC AND SURGICAL HAND DISINFECTION

(75) Inventors: Sabine Behrends, Pinneberg (DE); Peter Goroncy-Bermes, Hamburg (DE); Michael Mohr, Kaltenkirchen (DE); Burghard Puchstein, Hamburg (DE)

(73) Assignee: Air Liquide Sante (International), Paris (FR)

(*) Notice: Subject to any disclaimer, the term of this patent is extended or adjusted under 35 U.S.C. 154(b) by 36 days.

(21) Appl. No.: 09/878,283

(22) Filed: Jun. 12, 2001

(65) Prior Publication Data

US 2001/0036963 A1 Nov. 1, 2001

Related U.S. Application Data

(62) Division of application No. 09/297,459, filed as application No. PCT/EP97/06071 on Oct. 29, 1997, now abandoned.

(30) Foreign Application Priority Data

Nov. 5, 1996 (DE) .......................................... 196 47 692

(51) Int. Cl.$^7$ .......................... C07H 1/00; A61K 31/715
(52) U.S. Cl. .......................................... 536/124; 514/54
(58) Field of Search ............................. 536/124; 514/54

(56) References Cited

U.S. PATENT DOCUMENTS

| | | | |
|---|---|---|---|
| 4,206,215 A | 6/1980 | Bailey | 424/263 |
| 4,420,484 A | 12/1983 | Gorman et al. | 424/326 |
| 4,542,125 A | 9/1985 | Gorman et al. | 514/57 |
| 5,185,161 A | 2/1993 | Davidson et al. | 424/665 |
| 5,460,833 A | 10/1995 | Andrews et al. | 424/606 |
| 5,665,307 A | 9/1997 | Kirschner et al. | 422/28 |
| 5,750,733 A | 5/1998 | Vermeer | 549/346 |
| 5,880,076 A | 3/1999 | Vermeer | 510/123 |

FOREIGN PATENT DOCUMENTS

| | | |
|---|---|---|
| EP | 0161425 | 11/1985 |
| WO | WO-96/17929 A1 * | 6/1996 |

OTHER PUBLICATIONS

H. Janistyn, "Handbuch der Kosmetika und Riechestoffe", Dr. A. Huthig Verlag Heidelberg 1969, Bd. I, pp. 659–660.

* cited by examiner

*Primary Examiner*—James O. Wilson
*Assistant Examiner*—Everett White
(74) *Attorney, Agent, or Firm*—Young & Thompson

(57) ABSTRACT

A disinfectant composition and process for making the same. The composition comprises octenidine dihydrochloride, at least one $C_1$ to $C_8$-alkyl alcohol, at least one surfactant chosen among non-ionic or cationic surfactants, water and optionally at least one α-hydroxycarboxylic acid.

13 Claims, No Drawings

WASHING DISINFECTANT FOR HYGIENIC AND SURGICAL HAND DISINFECTION

This application is a division of Application No. 09/297,459, filed on Jun. 8, 1999 now abandoned. Application No. 09/297,459 is the national phase of PCT International Application No. PCT/EP97/06071 filed on Oct. 29, 1997 under 35 U.S.C. § 371. The entire contents of each of the above-identified applications are hereby incorporated by reference.

The importance of hand disinfection for preventing nosocomial infections in hospitals and medical practices has been undisputed since Semmelweis.

Particularly in non-German-speaking countries, hand disinfection by washing is still very important, both in the ward and in the operating theatre. There, it is traditionally clearly preferred to the so-called rub-in method using alcoholic products, since the hands can be simultaneously cleaned and disinfected with the preparations used.

The preparations for this field of use which are currently on the market contain, as a rule, chlorhexidine salts in a relatively large amount (4%) as residual active ingredients. The presence of such large amounts of active ingredients and the associated increased extent to which these active ingredients remain on the skin frequently result in skin intolerances which furthermore can scarcely be reduced by introducing additives. The nonionic surfactants frequently used in these preparations either have poor degradability (e.g. block polymers) or entail the potential danger of nitrosamine formation (e.g. amine oxides). For example, a commercially successful product is known which contains block polymers and amine oxides as surfactants in addition to the active ingredient chlorhexidine digluconate, which is present in a concentration of 4% by weight. It is also generally known that most members of these classes of surfactants cause the skin to dry out to an extreme extent and hence lead to poor skin tolerance of the formulations developed therefrom.

The cationic octenidine dihydrochloride has been used to date as an antimicrobial active ingredient in various products and is considered to be very thoroughly described.

For example, octenidine dihydrochloride has proved useful for years in skin and mucous membrane preparations.

However, the use of octenidine dihydrochloride in washing preparations has been prevented to date by the fact that it has not been possible to develop an acceptably skin-friendly product suitable for hygienic and surgical hand disinfection. In particular, the surfactants used in tests have either had an adverse effect on the efficacy of the octenidine or reduce the skin-friendliness to an unacceptable level.

It is therefore the object of the invention to provide a washing hand disinfectant for hygienic and surgical hand disinfection based on octenidine, which disinfectant is substantially more skin-tolerated than the known chlorhexidine formulations and at the same time has a good antimicrobial action comparable with that of the known formulations.

This object is achieved by a composition comprising octenidine dihydrochloride at least one $C_1$ to $C_8$-alkyl alcohol, at least one surfactant chosen among non-ionic or cationic surfactants, water and optionally at least one α-hydroxy-carboxylic acid The solution preferably comprises a) 0.1 to 4% by weight of octenidine dihydrochloride,
b) 5 to 35% by weight of $C_1$- to $C_8$-alkyl alcohol,
c) 0.5 to 45% by weight of nonionic or cationic surfactant or a mixture thereof and
d) 0 to 5% by weight of α-hydroxycarboxylic acid.

The amounts stated in the description are based in each case on the pure components.

By the choice of the residual active ingredient octenidine dihydrochloride, which has substantially better efficacy than chlorhexidine salts, the active ingredient concentration used in the formulation can be considerably reduced. Furthermore, the skin intolerance occurring in the case of residual active ingredients owing to the possible, considerably lower concentration of the active ingredient is likewise greatly reduced. With the use of octenidine dihydrochloride, the active ingredient concentration can be reduced, for example, by a factor of 10 or more. Octenidine dihydrochloride is extremely suitable for the desired field of use and has in particular a long-term action in surgical hand disinfection.

The good action of the octenidine dihydrochloride is possible, and is supported by, the additional and simultaneous use of $C_1$- to $C_8$-alkyl alcohols and nonionic and/or cationic surfactants which do not have the disadvantages of the abovementioned surfactants (poor degradability, nitrosamine formation) and/or do not adversely affect the efficacy of the active ingredients.

Ethanol, isopropanol or n-propanol or a mixture thereof is preferred as the $C_1$- to $C_8$-alkyl alcohol, preferably $C_1$- to $C_6$-alkyl alcohol and in particular $C_1$- to $C_4$-alkyl alcohol.

Nonionic surfactants preferred according to the invention are alkyl polyglycosides (APG), and cationic surfactants preferred according to the invention are quaternary betaines.

The alkyl polyglycoside is preferably a $C_8$- to $C_{20}$-alkylpolyglucoside, in particular a $C_8$- to $C_{16}$-

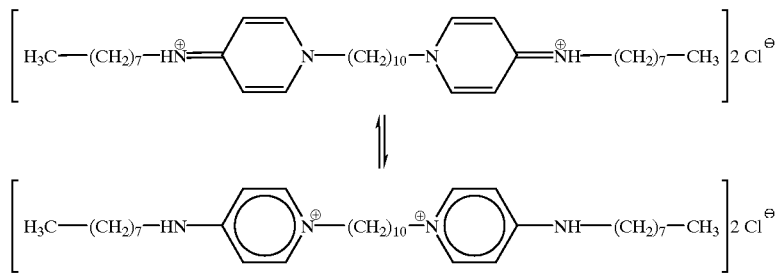

alkylpolyglucoside, a cocoylpolyglucoside, a laurylpolyglucoside, a decylpolyglucoside or a mixture thereof being preferred.

The idealized structure of the alkyl polyglycosides is as follows:

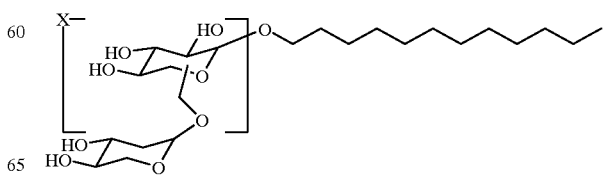

The C-chain length is 8–16 C atoms in the case of the cocoylpolyglucoside, 12–16 C atoms in the case of the laurylpolyglucoside and likewise 8–16 C atoms in the case of the decylpolyglucoside. Examples of mixtures of alkylpolyglucoside which can also be included in the compositions of the present application are described in the patent applications published under Number EP 0 553 241, WO 9513863, FR 2 734 496.

The quaternary betaine according to the invention is preferably the N-[N'(N"-2-hydroxyethyl-N"-carboxyethylaminoethyl)acetamido]-N,N-dimethyl-N-cocoylammonium betaine of the formula:

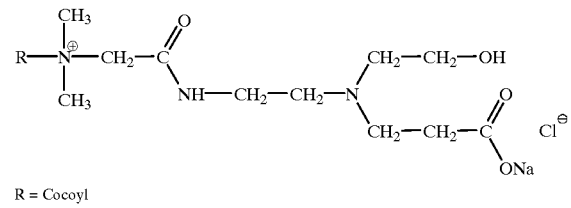

R = Cocoyl

However, the group R may in general be an alkyl group having 8 to 22, in particular 12 to 18, carbon atoms.

If an β-hydroxycarboxylic acid is used, the α-hydroxycarboxylic acid used according to the invention is lactic acid or mandelic acid, mandelic acid being preferred. The α-hydroxycarboxylic acid can also serve as a skin protection component and/or for adjusting the pH to, preferably, 2 to 7, in particular 3 to 6 and preferably about 5.

It is surprising that the good efficacy of the octenidine dihydrochloride is not influenced by the addition of the surfactants according to the invention, as has been shown to be the case, for example, as a result of the addition of ampholytic surfactants, such as cocamidopropyl betaine.

Table 1 below shows a comparison of the efficacy, in the surgical hand disinfection test according to the CEN Guideline, of this cocamidopropyl betaine-containing octenidine dihydrochloride formulation with a product which is obtainable on the market and contains chlorhexidine digluconate as the active ingredient in a concentration of 4% by weight and block polymer and amine oxide as surfactant (RF values):

TABLE 1

| Chlorhexidine digluconate formulation + block polymer + amine oxide | | Octenidine dihydrochloride formulation + cocamidopropyl betaine | |
|---|---|---|---|
| 3 min | RF = 0.99 | 3 min | RF = 0.61 |
| 3 h | RF = 0.66 | 3 h | RF = 0.01 |

Furthermore, it is surprising that the skin intolerances which are known to occur with the use of nonionic surfactants do not arise. This is particularly striking in the case of the preferably used alkyl polyglycosides, the skin intolerance in the case of the APGs being greater than in the case of the quaternary betaines and the degradability in the case of the APGs being greater than in the case of the quaternary betaines and this in turn being greater than in the case of the block polymers.

Further auxiliaries may be added to the composition according to the invention, for example skin protection agents, such as allantoin in an amount of, preferably, 0.1 to 0.3% by weight, so-called refatting agents, such as polyol fatty acid esters or lauryl alcohol with 2 moles of ethylene oxide in an amount of, preferably, 0.5 to 5% by weight, conditioners, such as polyquaternary ammonium compounds in an amount of, preferably, 0.5 to 5% by weight, thickeners, such as hydroxyethylcellulose or derivatives thereof in an amount of, preferably, 0.5 to 2.0% by weight, colorants in an amount of, preferably, 0.001 to 0.1% by weight or perfumes in an amount of, preferably, 0.05 to 1.0% by weight. The stated amounts are based on the total mixture.

For example, the following basic formulations A to C may be used as washing hand disinfectant:

Formulation A

| | |
|---|---|
| 10% by weight of | 1-propanol |
| 8% by weight of | 2-propanol |
| 0.3% by weight of | octenidine dihydrochloride |
| 1% by weight of | mandelic acid and |
| 10% by weight of | cocoylpolyglucose |
| Remainder | water |

Formulation B

| | |
|---|---|
| 10% by weight of | 1-propanol |
| 8% by weight of | 2-propanol |
| 0.3% by weight of | octenidine dihydrochloride |
| 1% by weight of | mandelic acid |
| 10% by weight of | N-[N'(N"-2-hydroxyethyl-N"-carboxyethylaminoethyl) acetamido]-N,N-dimethyl-N-cocoylammonium betaine |
| Remainder | water |

Formulation C

| | |
|---|---|
| 10% by weight of | 1-propanol |
| 8% by weight of | 2-propanol |
| 0.3% by weight of | octenidine dihydrochloride |
| 1% by weight of | mandelic acid |
| 10% by weight of | laurylpolyglucoside |
| Remainder | water |

The washing hand disinfectants according to the invention are prepared by initially introducing the alkyl alcohols and dissolving octenidine dihydrochloride therein. The surfactant and the mandelic acid are then added with stirring and, if desired, stirring is continued until a clear solution is obtained. The pH is adjusted to 5.0±0.2 with a base, such as NaOH, or an acid, such as mandelic acid.

The efficacy of these hand disinfectants according to the invention was tested analogously to the new CEN method in comparison with the abovementioned product obtainable on the market (containing chlorhexidine gluconate as active ingredient) and by a standard British method of Babb et al. (J. Hosp. Infec. (1991) 18 Supp. B, 41–49).

Surgical Hand Disinfection with Washing Preparations According to a Modified CEN Guideline (The modification consisted in the use of the chlorhexidine competitor product as reference solution instead of 60% strength by volume 1-propanol solution.)

1. Requirements

The average reduction in the microbial hand flora by treatment of the hands with the test solution for surgical hand washing may not be significantly smaller than the germ count reduction which is achieved using the reference solution (Hibiscrub®, Zeneca). The time of use is 3 minutes. The immediate effect and the long-term effect after 3 hours are then determined.

The reduction factors are determined from the differences between the preliminary and subsequent values, usually expressed by the logarithm to the base ten:

log RF=log preliminary value−log subsequent value

2. Test Subjects 20 test subjects with healthy skin and short fingernails are required for the test.

3. Determination of the Preliminary Values 10 ml of potash soap (20% w/v) are placed in the moistened hands which must be washed according to a specific procedure. In the latter, the following washing steps are performed, each of these steps comprising 5 back-and-forth movements and optionally the hands being changed. First, the palms of the hands are rubbed together. The palm of one hand is then rubbed against the back of the other hand. Next, the palms of the hands are again rubbed together, this time the fingers of the two hands being clasped together. The backs of the fingers of one hand are then rubbed against the palm of the other hand, the fingers of the two hands hooking into one another. Furthermore, the thumb of one hand is gripped by the other hand and, by means of rotary movements, rubbed against the palm of the hand forming the fist. Finally, the bent fingers of one hand are moved back and forth in a rotating manner in the palm of the other hand. After 30 seconds, the hands are rinsed off and dried. The preliminary values are then determined by massaging the fingertips.

4. Use of the Reference Solution 5 ml of Hibiscrub® are placed in the moistened hands which are washed according to the above scheme. After 1.5 minutes, a further 5 ml of the reference solution are pipetted onto the hands and rubbed for a further 1.5 minutes. Thereafter, the hands are rinsed off for 15 seconds and dried with paper hand towels for the determination of the subsequent values. One hand of the test subjects serves for determining the immediate value (3 minutes) and the other for determining the long-term action (3 hours) after wearing a glove.

5. Use of the Test Solution

This procedure is carried out according to the above method for the reference solution.

The test results obtained using the compositions according to the invention are summarized in Table 2 below.

TABLE 2

| 4% of chlorhexidine digluconate + block polymer + amine oxide | | 0.3% of octenidine dihydrochloride quaternary betaine | | 0.3% of octenidine dihyrochloride + APG | |
|---|---|---|---|---|---|
| 3 min | 3 h | 3 min | h | 3 min | 3 h |
| 0.88 | 0.53 | 0.80 | 0.82 | | |
| 0.88 | 0.53 | | | 0.92 | 0.75 |

Standard British Method According to Babb et al.

1. Determination of the Preliminary Values

The hands are washed, rinsed off and dried according to the scheme already described. Thereafter, a glove (Regent Biogel) is placed over each hand and filled with 50 ml of wash solution. After the gloves have been filled, the hands are massaged for 1 minute. To determine the germ count, at least 3 ml of the wash solution are taken by means of a pipette.

2. Use of the Reference and Test Solutions

Reference and test solutions are used as follows:

Wash hands for 30 seconds with potash soap

Rinse off for 15 seconds

Pipette 5 ml of solution into the hands and rub

Brush each hand, including fingernails, for 15 seconds

Wash hands and lower arm for 15 seconds

Rinse off for 15 seconds

Pipette 5 ml of solution into the hands and wash for 2 minutes according to the scheme already described Rinse off for 15 seconds Dry hands with paper hand towels One hand of the test subjects serves for determining the immediate value (3 minutes) and the other for determining the long-term action (3 hours) after wearing a glove. Germ recovery for determining the subsequent values is carried out as for the calculation of the preliminary values with the aid of gloves which are placed over the hands and filled with 50 ml of wash solution. After the hands have been massaged (1 minute), at least 3 ml are taken and are used for determining the germ count.

The test results obtained are summarized in Table 3 below.

TABLE 3

| 4% chlorhexidine digluconate + block polymer + amide oxide | | 0.3% octenidine dihydrochloride + APG | |
|---|---|---|---|
| 2 min 45 sec | 3 h | 2 min 45 sec | 3 h |
| 0.91 | 1.16 | 0.78 | 1.21 |

The efficacies of the preparations compared are approximately the same. However, the preparations according to the invention are better in terms of their skin tolerance.

We claim:

1. A method for disinfecting surgical hands for preventing nosocomial infections in hospital and medical practices comprising the steps of: applying an effective amount of a composition to said hands, wherein said composition has a pH of 3 to 6 and comprises octenidine dihydrochloride, at least one $C_1$ to $C_8$-alkyl alcohol, at least one surfactant chosen from $C_8$- to $C_{20}$-alkylpolyglucoside or a mixture thereof, and at least one α-hydroxycarboxylic acid.

2. The method according to claim 1, wherein the composition comprises:

0.1 to 4% by weight of octenidine dihydrochloride, 5 to 35% by weight of $C_1$- to $C_8$-alkyl alcohol, 0.5 to 45% by weight of nonionic surfactant or a mixture thereof, and up to 5% by weight of α-hydroxycarboxylic acid.

3. The method according to claim 1, wherein the composition comprises:

0.1 to 2% by weight of octenidine dihydrochloride, 10 to 30% by weight of $C_1$- to $C_8$-alkyl alcohol, 0.5 to 20% by weight of nonionic surfactant or a mixture thereof, and 0.1 to 2% by weight of α-hydroxycarboxylic acid.

4. The method according to claim 1, wherein the composition comprises:

0.1 to 0.5% by weight of octenidine dihydrochloride, 10 to 20% by weight of $C_1$- to $C_8$-alkyl alcohol, 5 to 15% by weight of nonionic surfactant or a mixture thereof, and 0.5 to 1.5% by weight of α-hydroxycarboxylic acid.

5. The method according to claim 1, wherein the $C_1$- to $C_8$-alkyl alcohol is a $C_1$ to $C_6$-alkyl alcohol.

6. The method according to claim 5, wherein the $C_1$- to $C_6$-alkyl alcohol is a $C_1$ to $C_4$-alkyl alcohol.

7. The method according to claim 1, wherein the α-hydroxycarboxylic acid is mandelic acid or lactic acid.

8. The method according to claim 1, wherein the composition comprises:

10% by weight of 1-propanol,
8% by weight of 2-propanol,
0.3% by weight of octenidine dihydrochloride,
1% by weight of mandelic acid, and
10% by weight of cocoylpolyglucoside.

9. The method according to claim 1, wherein the composition comprises: 10% by weight of 1-propanol,
8% by weight of 2-propanol,
0.3% by weight of octenidine dihydrochloride,
0.5% by weight of lactic acid, and
10% by weight of cocoylpolyglucoside.

10. The method according to claim 1, wherein the composition comprises:

10% by weight of 1-propanol,
8% by weight of 2-propanol,
0.3% by weight of octenidine dihydrochloride,
1% by weight of mandelic acid, and
10% by weight of laurylpolyglucoside.

11. The method according to claim 1, wherein the composition further comprises one or more compounds selected from the group consisting of skin protection agents, refatting agents, conditioners, thickeners, colorants, and perfumes.

12. A method for disinfecting the hands of a person comprising the step of applying to said hands an effective amount of a composition comprising octenidine dihydrochloride, at least one $C_1$ to $C_6$-alkyl alcohol, at least one surfactant chosen from among a $C_8$ to $C_{20}$-alkylpolyglucoside non-ionic surfactant and a cationic surfactant that is N-[N'(N"-2-hydroxyethyl-N"-carboxyethylaminoethyl)acetamido]-N,N-dimethyl-N-cocoylammonium betaine, water, and at least one α-hydroxycarboxylic acid.

13. A method for disinfecting the skin of a person comprising the steps of: applying an effective amount of a composition to said skin, wherein said composition has a pH of 3 to 6 and comprises octenidine dihydrochloride, at least one $C_1$ to $C_8$-alkyl alcohol, at least one surfactant chosen from $C_8$- to $C_{20}$-alkylpolyglucoside or a mixture thereof, and at least one α-hydroxycarboxylic acid.

* * * * *